United States Patent [19]
Biton et al.

[11] Patent Number: 5,834,452
[45] Date of Patent: Nov. 10, 1998

[54] 1- OR 6-HYDROXYLATED STEROIDS

[75] Inventors: Jacques Biton, La Croix Saint Quen; Jean-Pierre Marchandeau, Annet Sur Marne; Robert Azerad, Ris Orangis; Isabelle Lacroix, Choisy Le Roi, all of France

[73] Assignee: Roussel Uclaf, France

[21] Appl. No.: 861,975

[22] Filed: May 22, 1997

[30] Foreign Application Priority Data

May 22, 1996 [FR] France .................................. 96 06350

[51] Int. Cl.[6] .............................. A61K 31/575; C07J 9/00
[52] U.S. Cl. .................. 514/178; 552/541; 552/542; 552/548; 552/551; 552/553
[58] Field of Search ............................ 514/178; 552/541, 552/542, 548, 551, 553, 648

[56] References Cited

U.S. PATENT DOCUMENTS

| | | | |
|---|---|---|---|
| 4,273,771 | 6/1981 | Coussediere | 424/242 |
| 5,384,419 | 1/1995 | Buendia et al. | 552/556 |
| 5,399,685 | 3/1995 | Buendia et al. | 540/30 |
| 5,473,087 | 12/1995 | Buendia et al. | 552/556 |

*Primary Examiner*—Allen J. Robinson
*Assistant Examiner*—Barbara Badio
*Attorney, Agent, or Firm*—Bierman, Muserlian and Lucas

[57] ABSTRACT

A compound of the formula

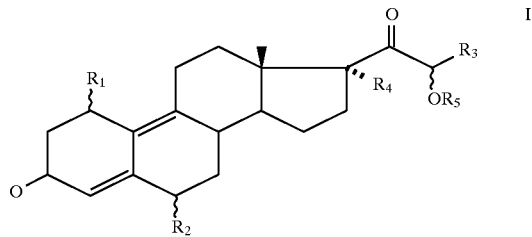

having progestomimetic activity, wherein the substituents are as defined in the specification and compositions of a compound of formula I and an estrogen compound.

16 Claims, No Drawings

1- OR 6-HYDROXYLATED STEROIDS

FIELD OF THE INVENTION

Novel 1- or 6-hydroxylated steroids and mixtures thereof with an estrogen compound having progestiomimetic activity.

OBJECTS OF THE INVENTION

It is an object of the invention to provide the novel compounds of formula I and a process for their preparation.

It is another object of the invention to provide novel progestiomimetic compositions and novel methods of inducing progestiomimetic activity in warm-blooded animals.

These and other objects and advantages of the invention will become obvious from the following detailed description.

THE INVENTION

The novel compounds of the invention have the formula

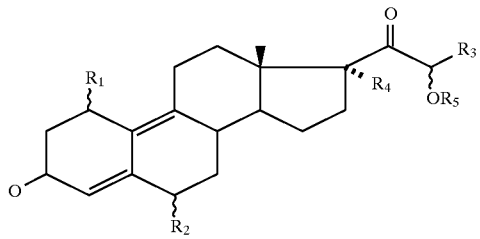

wherein $R_1$ is hydrogen and $R_2$ is —$OR_6$ or $R_1$ is —$OR_6$ and $R_2$ is hydrogen and $R_6$ and $R_5$ are individually selected from the group consisting of acyl of an organic carboxylic acid of 1 to 12 carbon atoms optionally substituted by at least one halogen and hydrogen and $R_3$ is alkyl of 1 to 12 carbon atoms, $R_4$ is alkyl of 1 to 4 carbon atoms, the wavy lines indicate the α- or β-position and that —$OR_5$ is in the 21R or 21S-position.

Examples of alkyl of 1 to 12 carbon atoms are methyl, ethyl, propyl, isopropyl, butyl, isobutyl, tert-butyl, n-pentyl, n-hexyl, 2-methylpentyl, 2,3-dimethylbutyl, n-heptyl, 2-methylhexyl, 2,2-dimethylpentyl, 3,3-dimethylpentyl, 3-ethylpentyl, n-octyl, 2,2-dimethylhexyl, 3,3-dimethylhexyl, 3-methyl-3-ethylpentyl, nonyl, 2,4-dimethylheptyl and n-decyl. Examples of alkyl of 1 to 4 carbon atoms are methyl, ethyl, propyl, isopropyl, butyl, isobutyl and tert-butyl.

Examples of acyl an organic carboxylic acid of 1 to 12 carbon atoms are formyl, acetyl, propionyl, butyryl, isobutyryl, valeryl, isovaleryl, succinyl, pivaloyl and benzoyl. When they are substituted by halogen, it is preferably chlorine or iodine or fluorine. Examples include chloracetyl, dichloracetyl, trichloracetyl and trifluoroacetyl.

Among the preferred compounds of formula I are those wherein $R_3$ and $R_4$ are methyl, those wherein $R_1$ is hydrogen and $R_2$ is hydroxy, those wherein $R_1$ is hydroxy and $R_2$ is hydrogen. Examples of specific preferred compounds are [17β-(S)-1-hydroxy-17-(2-hydroxy-1-oxopropyl)-17-methyl-$\Delta^{4,9}$-estradiene-3-one and [17β-(S)]-6-hydroxy-17-(2-hydroxy-1-oxopropyl)-17-methyl-$\Delta^{4,9}$-estradiene-3-one in any of 1α-OH, 1β-OH, 6α-OH and 6β-OH stereoisomeric forms or mixtures thereof.

The process of the invention for the preparation of a compound of formula I comprises subjecting a compound of the formula

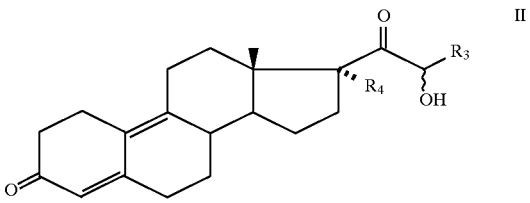

wherein $R_3$, $R_4$ and the wavy lines are defined as above to a bioconversion by culturing with filamentous fungi and optionally separating out the 1-OH and 6-OH products or esterifying the hydroxylated compounds.

Examples of filamentous fungi useful for the preparation of the 1-OH and 6-OH steroids are

| | |
|---|---|
| Aspergillus terreus | MMP 2296 |
| Cuninghamella baineri | ATTC 9244 |
| Cuninghamella elegans | ATTC 26269 |
| Cuninghamella elegans | ATTC 36112 |
| Mortierella isabellina | NRRL 1757 |
| Mortierella isabellina | MMP 108 |
| Rhizopus arrhizus | ATCC 11145 |
| Thamnostylum piriforme | ATCC 8992 |
| Fusarium roseum | ATCC 14717 |

For the preferential production of 1-OH:

| | |
|---|---|
| Cuninghamella baineri | ATTC 9244 |
| Mortierella isabellina | MMP 108 |
| For the preferential production of 6-OH: | |
| Mortierella isabellina | NRRL 1757 |
| Fusarium roseum | ATCC 14717 |

Origin of strains:
ATCC: American Type Culture Collection, Rockville, Md., USA.
MMP: Mycothèque du Muséum d'Histoire Naturelle, Paris,
NRRL: Northern Utilization Research and Development Division, Peoria, Ill., USA.

The hydroxylation is carried out by known methods for microbiological hydroxylation of steroids using cultures of fungi (ref.: "Microbial conversions of steroids and alkaloids", Iizuka et al, publishers, University of Tokyo Press, Springer Verlag, Berlin, 1981). Thus, the most favorable fermentation conditions are first determined by analytical route, in particular by thin layer chromatography or HPLC, in general common preliminary tests, such as the most favorable choice of nutrient medium, the appropriate substrate solvent, the concentration of substrate, technical conditions such as temperature, aeration, pH, and the optimum periods for germination, the addition of substrate and the contact of the substrate with the microorganism.

It appears that it is advantageous to use concentrations of approximately 40 to 2,000 mg of substrate per liter of nutrient medium. The value of the pH is preferably adjusted to a value of the order of 5 to 7. The temperature of the culture is of the order of 20° to 40° C., preferably from 25° to 35° C. For aeration, approximately 1 liter of air per minute per liter of culture broth is provided. The conversion of the substrate is advantageously monitored by analysis using thin layer chromatography of extracted samples, or using HPLC. In general, after 24 to 144 hours, sufficient quantities of hydroxylated steroids have formed.

The isolation, separation and purification of the products of the process is carried out in a manner known per se. For example, the products of the process can be extracted with an organic solvent such as ethyl acetate, the extract is evaporated, separated and the products are purified by column chromatography.

Preferably, the filamentous fungi is selected from the following strains:

| | |
|---|---|
| Cuninghamella baineri | ATTC 9244 |
| Mortierella isabellina | NRLL 1757 or MMP 108 |
| Fusarium roseum | ATCC 14717. |

The preferred compound of formula II is trimegestone or [17β-(S)]-17-(2-hydroxy-1-oxopropyl)-17-methyl-$\Delta^{4,9}$-estradiene-3-one and the preferred filamentous fungi is Cuninghamella baineri, Mortierella isabellina or Fusarium roseum to obtain as the 1-hydroxylated and 6-hydroxylated derivatives:

[17β-(S)]-1-hyroxy-17-(2-hydroxy-1-oxopropyl)-17-methyl-$\Delta^{4,9}$-estradiene-3-one and [17β-(S)]-6-hyroxy-17-(2-hydroxy-1-oxopropyl)-17-methyl-$\Delta^{4,9}$-estradiene-3-one which are subsequently separated.

A more preferred mode of the process comprises culturing trimegestone with Cuninghamella baineri ATCC 9244 to obtain the 1-hydroxylated derivative:

[1α, 17β-(S)]-1-hydroxy-17-(2-hydroxy-1-oxopropyl)-17-methyl-$\Delta^{4,9}$-estradiene-3-one or [1β, 17β-(S)]-1-hydroxy-17-(2-hydroxy-1-oxopropyl)-17-methyl-$\Delta^{4,9}$-estradiene-3-one, alone or in a mixture.

The optional subsequent esterification of the free hydroxyl groups is carried out according to processes which are commonly used in the chemistry of steroids for the esterification of secondary and tertiary hydroxy groups. As an appropriate esterification process, there can be mentioned the reaction of steroids with acid anhydrides or chlorides in the presence of basic catalysts such as sodium or potassium bicarbonate, potassium carbonate, sodium or potassium hydroxide, pyridine, lutidine, collidine or 4-dimethylaminopyridine.

The progestomimetic compositions of the invention are comprised of a progestomimetically effective amount of a compound of formula I, and optionally an estrogen compound and an inert pharmaceutical carrier. The compositions may be in the form of tablets, dragees, capsules, granules, suppositories, ovules, microspheres, nanospheres, implants, patches, ointments, creams, gels and injectable solutions.

The compounds of formula I have no affinity vis-a-vis estrogen, androgen, glucocorticoid and mineralocorticoid receptors. The compositions are useful for the treatment of gynecological problems caused by a luteal insufficiency: menstrual irregularity due to ovulation problems, dysmenorrhea, premenstrual syndrome, mastodynia, functional hemorrhages and menorrhagia of the fibroma, problems relating to menopause, sterility, ovarian dystrophies due to inactivity of the ovaries and in the treatment of tumors of the breast and the uterus.

The combination of the products of formula I with estrogens finds use in hormonal replacement treatment relating to menopause and particularly in the prevention or treatment of osteoporosis.

Among the preferred estrogens there can be mentioned 17β-estradiol and its esters such as estradiol valerate, cyprionate, decanoate and acetate, ethynyl estradiol, estrone, estrogen "of equine origin" such as Premarin$^R$, or a combination of these compounds. The combination estrogen/product of formula I also finds use as a contraceptive. The preferred estrogen will then be ethynyl estradiol.

The novel method of inducing progestomimetic activity in warm-blooded animals comprises administering to warm-blooded animals an antiprogestomimetically effective amount of a compound of formula I and optionally an estrogen compound. The compounds may be administered orally, parenterally, rectally or topically. The usual daily dose is 0.01 to 10 mg/kg depending on the particular compound, the method of administration and the condition being treated.

Examples of pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compounds of formula II used as starting products of the process of the invention are described in European Patent EP 0007823 and the strains used in the process of the invention are known.

In the following examples, there are described several preferred embodiments to illustrate the invention. However, it is to be understood that the invention is not intended to be limited to the specific embodiments.

EXAMPLE 1

Production/purification of 1α-OH trimegestone

A solid nutrient medium for 1 liter of distilled water, 20 g of glucose, 5 g of pancreatic peptone, 5 g of yeast extract, 5 g of malt extract and 20 g of bactoagar was inoculated with a lyophilized strain of Cuninghamella baineri (ATCC 9244). The mixture was incubated under sterile conditions for 7 days at 25° C. in an oven. At the end of 7 days, the spores were harvested and these fresh spores were used to seed two 2-liter Erlenmeyer flasks, each of which contained 800 ml of a nutrient solution sterilized for 30 minutes in an autoclave.

This nutrient medium contained 10 g of corn steep, 2 g of $NaNO_3$, 0.5 g of $MgSO_4$, $7H_2O$, 0.02 g of $FeSO_4$, $7H_2O$ and 0.5 g of KCl for 900 ml of distilled water. At the time of seeding, a sterile Phosphate buffer solution ($K_2HPO_4$, 2 g; $KH_2PO_4$, 1 g in 40 ml of water) was added and a nutrient complement in the form of 60 ml of a sterilized aqueous solution containing 30 g of glucose.

The culture was left to develop at 270° C. with stirring at 200 revs/minute in a rotary shaker. After 65 hours, a solution of 400 mg of trimegestone in 5 ml of 99% ethanol was added to each Erlenmeyer flask. After total conversion of the substrate used (72 hours of contact), the incubation medium was filtered and the filtrate was saturated by the addition of a large excess of NaCl. The solution saturated with NaCl was then extracted three times with stirring using 250 ml of ethyl acetate. After drying over $MgSO_4$, the extract was evaporated under vacuum at a bath temperature of 40° C. to obtain 965 mg of a yellowish oil. This oil was chromatographed on a 60H silica gel column (Merck, 70–230 Mesh) using a mixture of methylene chloride/isopropanol (95:5) and 5 main fractions were obtained. The 209 mg fraction containing a majority of product A was purified by semi-preparative high pressure liquid chromatography (250×21.2 mm), in C18 bonded reversed phase, with a methanol/water mixture (50/50).

After evaporation of the solvent under vacuum at a bath temperature of 40° C., 84 mg of [1α, 17β-(S)]-1-hydroxy-17-(2-hydroxy-1-oxopropyl)-17-methyl-$\Delta^{4,9}$-estradiene-3-one (product A) were obtained, with a chromatographic purity higher than 96%. $^1H$ and $^{13}C$ NMR analyses: see Tables 1 and 2.

EXAMPLE 2

Production/purification of 6β-OH-trimegestone

A solid nutrient medium constituted by, for 1 liter of distilled water, 20 g of glucose, 5 g of pancreatic peptone, 5 g of yeast extract, 5 g of malt extract and 20 g of bactoagar was inoculated with a lyophilized strain of Mortierella isabellina (NRRL 1757). The mixture was incubated under sterile conditions for 7 days at 25° C., in an oven.

At the end of 7 days, the spores were harvested and these fresh spores were used to seed five 240 ml Erlenmeyer flasks, each of which contained 100 ml of a nutrient solution sterilized for 30 minutes in an autoclave. This nutrient medium contained: 10 g of corn steep, 2 g of $NaNO_3$, 0.5 g of $MgSO_4$, $7H_2O$, 0.02 g of $FeSO_4$, $7H_2O$, 0.5 g of KCl for 900 ml of distilled water. At the time of seeding, a sterile Phosphate buffer solution was added ($K_2HPO_4$), 2 g; $KH_2PO_4$, 1 g in 40 ml of water) and a nutrient complement in the form of 60 ml of a sterilized aqueous solution containing 30 g of glucose.

The culture was left to develop at 27° C. with stirring in a rotary shaker. After 60–66 hours, a solution of 50 mg of trimegestone in 1 ml of 99% ethanol was added to each Erlenmeyer flask. After total conversion of the substrate used (48 hours of contact), filtration was carried out through a cloth filter to separate the mycelium of the fermentation broth. The mycelium was then amply washed with distilled water and the filtrate of the washing and the filtered fermentation broth were combined. Then, the "washing filtrate/filtered broth" mixture was saturated by the addition of a large excess of NaCl.

The solution saturated with NaCl was then extracted three times with stirring using 250 ml of ethyl acetate and the extract was evaporated under vacuum at a bath temperature of 40° C. To clean the extract of secondary product resulting from the fermentation, chromatography was carried out on a 60H silica gel column (Merck, 230–400 Mesh) using a mixture of methylene chloride/methanol (95-5). The fractions obtained were collected into a single fraction, having an oily appearance. Finally, purification was carried out by semi-preparative high pressure liquid chromatography (250×21,2 mm), in C18 bonded reversed phase, with a methanol/water mixture (60/40). After evaporation under vacuum of the solvent of the useful fraction, at a bath temperature of 40° C., 21 mg of [6β, 17β-(S)]-6-hydroxy-17-(2-hydroxy-1-oxopropyl)-17-methyl-$\Delta^{4,9}$-estradiene-3-one (product B) were obtained with a chromatographic purity higher than 90%. $^1H$ and $^{13}C$ NMR analyses: see Tables 1 and 2.

EXAMPLE 3

Production/purification of 1α-OH-trimegestone and 6β-OH trimegestone

Five 500 ml Erlenmeyer flasks were prepared, each of which contained 90 ml of a nutrient solution No. 1. This nutrient medium contained 10 g of corn steep, 2 g of $NaNO_3$, 0.5 g of $MgSO_4$, $7H_2O$, 0.02 g of $FeSO_4$, $7H_2O$, 0.5 g of KCl and SQF 900 ml of distilled water. Similarly, a Schott flask was prepared containing a nutrient solution No. 2 containing 10 g of $K_2HPO_4$, 5 g of $KH_2PO_4$ and SQF 200 ml of demineralized water. Also a Schott flask was prepared containing a nutrient solution No. 3 containing 150 g of glucose and SQF 300 ml of demineralized water. In practice, 150 g of glucose were dissolved warm under strong stirring in 150 ml of demineralized water. After complete dissolution, the volume was adjusted to 300 ml for the test. The 5 Erlenmeyers and 2 Schott flasks were sterilized for 30 minutes at 121° C. in an autoclave.

Just before seeding the precultures, 4 ml of solution No. 2 and 6 ml of solution No. 3 were added under sterile conditions to each of the Erlenmeyers containing 90 ml of nutrient solution No. 1. Then, inoculation was carried out with 1 ml of frozen inoculum of the strain Fusarium roseum (ATCC 14717). The 5 Erlenmeyers were stirred at 200 revs/minute for 48 hours at a temperature of 27° C. in an orbital shaker having an orbit size of 2.5 cm.

With this preliminary culture, a 3-liter fermentor was inoculated which contained nutrient solution A, namely: 30 g of corn steep liquor, 6 g of $NaNO_3$, 1.5 g of $MgSO_4$, $7H_2O$, 0.06 g of $FeSO_4$, $7H_2O$, 1.5 g of KCl and SQF 2650 ml of demineralized water. The fermentor was then sterilized in the autoclave for 45 minutes at 121° C. Then, a 500 ml introduction flask was prepared containing 300 ml of solution B which was prepared as follows: 150 ml of distilled water were placed in a 500 ml beaker containing a magnetic stirrer, and stirring was carried out while warm. Then, 90 g of glucose were introduced slowly. After complete dissolution, 6 g of $K_2HPO_4$, then 3 g of $KH_2PO_4$ were added and the volume was adjusted to 300 ml with distilled water (test). The flask was then sterilized in the autoclave for 30 minutes at 121° C.

Before seeding, 300 ml of solution were introduced under sterile conditions into the fermentor. Then, inoculation was carried out with 50 ml of the preculture using an inoculation flask. The fermentation was taken to a temperature of 27° C., with a pressure of 0.3 bar, an initial stirring of 200 rpm and an aeration of 90 nl/h, namely 0.50 vvm. The partial pressure of oxygen was regulated to 50% and the pH was adjusted to 6.5, using 1M sulfuric acid up to 28 hours. It then developed freely until the end of the bioconversion.

At the end of 46 hours, after the active growth phase, 6 g of trimegestone were dissolved in 70 ml of acetone and then added under sterile conditions to the cell suspension. The culture was then continued under the same conditions. After 96 hours, the fermentation was stopped and filtration was carried out through a cloth filter to separate the mycelium from the fermentation broth. The mycelium was then amply washed in distilled water and the filtrate of the washing and the filtered fermentation broth were combined. The solution saturated with NaCl was extracted three times with stirring with 500 ml of ethyl acetate and once with 500 ml of methylene chloride. The combined organic fractions were distilled to dryness under vacuum at a bath temperature of 40° C.

The dry extract obtained was purified by preparative high pressure liquid chromatography in normal phase, on 10 u spherical silica in a methylene chloride/methanol mixture (95-5). Several fractions were obtained, 2 of which contained product A and product B. After evaporation of the solvent under vacuum at a bath temperature of 40° C., the following were obtained:

[1α, 17β-(S)]-1-hydroxy-17-(2-hydroxy-1-oxopropyl)-17-methyl-$\Delta^{4,9}$-estradiene-3-one/17β-estradiol (product A)- and [6β, 17β-(S)]-6-hydroxy-17-(2-hydroxy-1-oxopropyl)-17-methyl-$\Delta^{4,9}$-estradiene-3-one/17β-estradiol (product B) with a chromatographic purity of higher than 90%.

$^1H$ and $^{13}C$ NMR analyses: see Tables 1 and 2.

TABLE 2

| | 13C NMR of 2 metabolites of trimegestone (69.2 MHz, $CDCL_3$) | | |
|---|---|---|---|
| Carbon n° | Trimegestone | 6β-OH Trimegestone Product B | 1α-OH Trimegestone Product A |
| 1 | 25,6 | 25,9 | 65,9 |
| 2 | 36,9 | 37,3 | 45,5 |
| 3 | 199,5 | 200,2 | 197,6 |
| 4 | 122,1 | 122,3 | 121,5 |
| 5 | 156,9 | 155,4 | 154,3 |
| 6 | 30,7 | 68,4 | 31,0 |

TABLE 2-continued

13C NMR of 2 metabolites of trimegestone (69.2 MHz, CDCL$_3$)

| Carbon n° | Trimegestone | 6β-OH Trimegestone Product B | 1α-OH Trimegestone Product A |
|---|---|---|---|
| 7 | 27,6 | 34,3 | 27,3 |
| 8 | 39,4 | 34,6 | 39,7 |
| 9 | 145,4 | 145,3 | 150,6 |
| 10 | 125,5 | 122,7 | 127,9 |
| 11 | 25,7 | 25,7 | 25,4 |
| 12 | 32,8 | 33,0 | 33,0 |
| 13 | 45,1 | 45,4 | 45,1 |
| 14 | 51,0 | 50,6 | 51,4 |
| 15 | 24,0 | 30,7 | 30,3 |
| 16 | 30,8 | 24,0 | 23,9 |
| 17 | 60,0 | 60,0 | 60,0 |
| 18 | 15,7 | 15,8 | 15,8 |
| 19 | 21,5 | 21,7 | 21,6 |
| 20 | 217,0 | 217,2 | 217,1 |
| 21 | 69,6 | 69,7 | 69,7 |
| 22 | 22,0 | 22,1 | 21,6 |

TABLE 1

$^1$H NMR of 2 metabolites of trimegestone (250 MHz, CDCL$_3$; d in ppm, J in Hz). This table collects together the results obtained. The majority of the attributions described were carried out after study of the 2D 1H—1H or 1H-13C correlations.

| | Trimegestone | 6β-OH Trimegestone Product B | 1α-OH Trimegestone Product A |
|---|---|---|---|
| 1α and 1β | | 2, 6 (m) and 2, 9 (m) | — 5, 10 (br.s) |
| 2α and 2β | | 2, 5 (m) | 2, 6 (m) and 2, 7 (m) |
| 4 | 5, 67 (s) | 5, 82 (s) | 5, 76 (s) |
| 6α and 6β | | 4, 37 (dd) J = 3, 5 | 2, 4 (m) and 2, 6 (m) |
| 7α and 7β | | 1, 5 (ddd) and 2, 1 (m) | 1, 45 (m) and 1, 9 (m) |
| 8β | | 2, 6 (m) | 2, 3 (m) |
| 11α and 11β | | 2, 2 (dt) and 2, 8 (m) | 2, 4 (m) and 3, 0 (dm) |
| 12α and 12β | | 1, 7 (m) and 2, 0 (m) | 1, 7 (m) and 2, 05 (m) |
| 14β | | 1, 68 (m) | 1, 80 (m) |
| 15α and 15β | | 1, 4 (m) and 2, 7 (m) | 1, 4 (m) and 2, 7 (m) |
| 16α and 16β | | 1, 4 (m) and 1, 8 (m) | 1, 4 (m) and 1, 8 (m) |
| 18 | 0, 81 (s) | 0, 84 (s) | 0, 85 (s) |
| 19 | 1, 16 (s) | 1, 15 (s) | 1, 16 (s) |
| 21 | 4, 41 (q) J = 6, 4 | 4, 40 (q) J = 6, 4 | 4, 40 (q) J = 6, 4 |
| 22 | 1, 31 (d) J = 6, 4 | 1, 30 (d) J = 6, 4 | 1, 31 (d) J = 6, 4 |

Pharmacological study

1—Study of the activity of the products on hormonal receptors.

The human recombinant receptor (HGR, HPR, HAR, HMR, HER) was used.

Human progesterone receptor (HPR):

The recombinant human progestogen receptor was obtained by the superexpression in a cell system of insects—Baculovirus, according to the methodology described by Webb et al (Journal of Methods in Cell and Molecular Biology, (1990) Vol. 2 No. 4, p. 173–188) and the application of which was described for the expression of human hormonal receptors, for example the human glucocorticoid receptor (Srinivasan et al, Molecular Endocrinology, (1990) Vol. 4 No. 2, p. 209–216.

The BaculoGold Transfection Kit (PharMingen, reference 21000K) was used to insert the cDNA fragment described by Kastner et al (The EMBO Journal, (1990), Vol. 9 No. 5, p. 1603–1614), containing the region coding for the human progestogen receptor and to prepare the corresponding recombinant virus. The recombinant virus obtained in this way was used to express the progestogen receptor in SF9 insect cells (ATCC CRL1711), according to the known methodology cited previously.

$2 \times 10^7$ to $2.5 \times 10^7$ SF9 cells were cultured in a 175 ml "Falcon" flask in the TNM-FH medium supplemented with 10% fetal calf serum (FCS) and with 50 micrograms/ml of gentamycin. After infection, then incubation at 27° C. for 40 to 42 hours, the cells were taken up in 1 ml of lysis buffer (1), lysed by 2 cycles of freezing-thawing (−80° C./ 0° C.), then centrifuged at 4° C. for 30 minutes at 20,900 g. The supernatant, containing the recombinant human progestogen receptor, was stored in liquid nitrogen in quantities of 1 ml.

The supernatant was diluted at the time of use with 10 mM Tris buffer, 0.25M saccharose, HCl pH 7.4 containing 0.1% of gelatin and then incubated at 0° C. for 24 hours with a constant concentration (T) of tritiated 17α, 21-dimethyl-19-nor-$\Delta^{4,9}$ pregnadiene-3,20-dione in the presence of increasing concentrations of either unlabelled progesterone (0–2500×10$^{-9}$M), or the unlabelled product to be tested (1 to 25000×10$^{-9}$M). The concentration of bound tritiated 17,21-dimethyl-19-nor-$\Delta^{4,9}$-pregnadiene-3,20-dione (B) was then measured in each incubate using the charcoal dextran adsorption technique.

Human glucocorticoid receptor (HGR):

A supernatant of SF9 cells containing the recombinant human glucocorticoid receptor was obtained by the process described above for the progestogen receptor using the cDNA fragment described by Hollenberg et al (Nature, (1985), Vol. 318 No. 19/26 635) containing the region coding for the human glucocorticoid receptor. The cells obtained were lysed in the lysis buffer (2).

The supernatant was incubated at 0° C. for 24 hours with a constant concentration (T) of tritiated 11β, 17β-dihydroxy-6,21-dimethyl-$\Delta^{4,6}$-pregnatriene-20-yn-3-one in the presence of increasing concentrations of either unlabelled dexamethasone (0–1000×10$^{-9}$M), or the unlabelled product to be tested (1 to 25000×10$^{-9}$M). The concentration of bound tritiated 11β, 17β-dihydroxy-6,21-dimethyl-$\Delta^{1,4,6}$-pregnatriene-20-yn-3-one (B) was then measured in each incubate using the charcoal dextran adsorption technique.

Human estrogen receptor (HOR):

A supernatant of SF9 cells containing the recombinant human estrogen receptor was obtained by the process described above for the progestogen receptor using the cDNA fragment described in the expression vector HEGO by Tora et al (The EMBO Journal, (1989), Vol. 8 No. 7, p. 1981–1986) containing the region coding for the human estrogen receptor of "wild type" with a glycine in position 400. The cells obtained were lysed in the lysis buffer (1).

The supernatant was incubated at 0° C. for 24 hours with a constant concentration (T) of tritiated estradiol in the presence of increasing concentrations of either unlabelled estradiol (0–1000×10$^{-9}$M), or the unlabelled product to be tested (1 to 25000×10$^{-9}$M). The concentration of bound tritiated estradiol (B) was then measured in each incubate using the charcoal dextran adsorption technique.

Human androgen receptor (HAR)

A supernatant of SF9 cells containing the recombinant human androgen receptor was obtained by the process described above for the progestogen receptor using the cDNA fragment containing the region coding for the human androgen receptor. The cells obtained were lysed in the lysis buffer (3). The supernatant was incubated at 0° C. for an incubation time of 24 hours with a constant concentration (T) of tritiated testosterone in the presence of increasing concentrations of either unlabelled testosterone (0 to 1000× 10$^{-9}$M), or the unlabelled product to be tested (1 to 25000× 10$^{-9}$M). The concentration of bound tritiated testosterone (B) was then measured in each incubate using the charcoal dextran adsorption technique.

Human mineralocorticoid receptor (HMR):

A supernatant of SF9 cells containing the recombinant human mineralocorticoid receptor was obtained according to the process described above for the progestogen receptor using the cDNA fragment described by Baulieu et al (Proc. Natl. Acad. Sci., (1991), Vol. 88, p. 10681–10685) containing the region coding for the human mineralocorticoid receptor. The cells obtained were lysed in the lysis buffer (4). The supernatant was incubated at 0° C. for 24 hours with a constant concentration (T) of tritiated aldosterone in the presence of increasing concentrations of either unlabelled aldosterone (0 to 1000×10$^{-9}$M), or the unlabelled product to be tested (1 to 25000×10$^{-9}$M). The concentration of bound tritiated aldosterone (B) was then measured in each incubate using the charcoal dextran adsorption technique.

| Lysis buffers: | | |
| --- | --- | --- |
| (1) Tris-HCl pH 8 | | 20 mM |
| EDTA | | 0.5 mM |
| KCl | | 400 mM |
| Glycerol | | 20% |
| Added extemporaneously: | | |
| DTT | | 2 mM |
| PIC* mixture | | 1% |
| (2) KH$_2$PO$_4$, NaOH pH 7 | | 50 mM |
| Glycerol | | 20% |
| Added extemporaneously: | | |
| DTT (Dithiothreitol) | | 5 mM |
| Sodium molybdate | | 20 mM |
| PIC* mixture | | 0.1% |
| *-continued* | | |
| Lysis buffers: | | |
| (3) Tris-HCl pH 7.5 | | 20 mM |
| EDTA, 2H$_2$O | | 1 mM |
| Glycerol | | 10% |
| Added extemporaneously: | | |
| PMSF (Phenyl methyl sulphonyl fluoride) | | 0.1 mM |
| Sodium molybdate | | 20 mM |
| PIC* mixture | | 0.1% |
| (4) Tris-HCl pH 7.4 | | 20 mM |
| EDTA, 2H$_2$O | | 1 mM |
| Glycerol | | 10% |
| Added extemporaneously: | | |
| Sodium tungstate | | 20 mM |
| PIC* mixture | | 0.1% |

*PIC* mixture: Leupeptin, Pepstatin A, Aprotinin, Antipaine, Chymostatin (Each peptide at a final concentration of 2.5 ug/ml).

Expression of Results and Calculation Methods
Calculation of the relative bond affinity (RBA).

The following two curves were drawn: the percentage of bound tritiated hormone B/BO as a function of the logarithm of the concentration of unlabelled reference hormone or as a function of the logarithm of the concentration of unlabelled test product. The straight line of the following equation was determined:

$$I_{50}=100(B_o/B_o+B\min/B_o)/2 \text{ i.e.}$$

$$I_{50}=100(1+B\min/B_o)/2=50(1+B\min/B_o)$$

$B_o$=concentration of bound tritiated hormone in the absence of any unlabelled product.

B min=concentration of bound tritiated hormone in the presence of the highest concentration of unlabelled reference hormone.

The intersections of the straight line $I_{50}$ and the curves allowed the evaluation of the concentrations of unlabelled reference hormone (CH) and of the unlabelled test product (CX) which inhibited by 50% the specific binding of the tritiated hormone on the receptor.

The relative bond affinity (RBA) of the test product was determined by the equation:

$$RBA=100(CH/CX)$$

The RBA's of reference products Estradiol, Progesterone Dexamethasone, Testosterone and Aldosterone were arbitrarily taken as being equal to 100. The results of the RBA's obtained are as follows:

| Products | Human glucocorticoid receptor 24 h at 0° C. Dexamethasone = 100 | Human progestogen receptor 24 h at 0° C. Progesterone = 100 | Human androgen receptor 24 h at 0° C. Testosterone = 100 | Human mineralocorticoid receptor 24 h at 0° C. Aldosterone = 100 | Human estrogen receptor 24 h at 0° C. Estradiol = 100 |
| --- | --- | --- | --- | --- | --- |
| Trimegestone | 14 | 588 | 2, 5 | 28 | 0 |
| 1α-OH Product A | 0, 06 | 64 | 0, 04 | 0, 1 | 0 |
| 6β-OH Product B | 0, 05 | 12 | 0 | 0, 3 | 0 |

The products whose RBA was equal to 0 have an $IC_{50}$ greater than 25000 nM.

Conclusion:

Product A (α-OH) had a good relative bond affinity (RBA) for the human progestogen receptor, although this was 9 times weaker than that of Trimegestone. On the other hand, product B (6-OH) only had a moderate RBA for this receptor. Contrary to Trimegestone which showed moderate RBA's for the human glucocorticoid and mineralocorticoid receptors of humans, and a weak RBA for the human androgen receptor, these 2 products only had no or negligible RBA's for these receptors. The RBA's for the human estrogen receptor, were zero for Trimegesterone and products A and B.

2. —Determination of the progestomimetic activity of the products of the invention: Endometrial transformation in the rabbit.

a) Method

The animals used were impuberal female rabbits which were 40–45 days old. The animals were treated with estradiol (5 ug/0.2 ml/rabbit in solution of corn oil, 10% ethanol) by subcutaneous route from day 1 to day 5, then the product to be studied was administered from day 8 to day 11. On day 12, the animals were sacrificed and a median portion of each uterine cornua was removed from each animal and fixed in Bouin's liquid for histological study. After fixing, the samples were dehydrated, included, cut, mounted, the paraffin was removed and then the sample was stained with hemalum-eosin-saffron.

b) Histology

The sections were examined under light-optical microscopy, first, with low magnification, to ensure that morphological variations did not exist between them. Then, for each of the cornua, a semi-quantitative evaluation of the endometrial proliferation (uterine lace) was carried out by the McPhail scale from 0 to 4 with 0.5 intermediates and the two figures were averaged. Similarly, the degree of hypertrophy of the cornua was evaluated by the same scale. At higher magnification, morphological observations of the mucous membrane or the myometrium could possibly be formulated.

c) Retained protocol.

The 1-OH metabolite (product A) was tested at doses of 10, 100, 1000 μg/kg by subcutaneous route as well as orally at a dose of 1000 μg/kg. The 6-OH metabolite (product B) was tested at doses of 100, 1000 and 10000 μg/kg subcutaneously. As a control, progesterone was administered at doses of 100 and 1000 μg/kg by subcutaneous route.

d) References.

Clauberg, C.

Zur Physiologie und Pathologie des Sexual Hormone, im besonderen des Hormons des Corpus-Luteum 1. Mitt. : Der biologishe Test für das luteohormon am infantilen Kaninchen. Zentralbl. Gynakol. 1930, 54: 2757–70.

Mc Phail, M. K.

The assay of progestins

J. Physiol (London) 1934, 83: p. 145–56.

Note: Trimegestone had a progestomimetic activity, in this test, starting from a dose of 1 μg/kg and a strong activity at doses of 3 and 10 μg/kg orally and 3 μg/kg percutaneously. On the other hand, the maximal activity of progesterone on the uterine lace was situated at 1000 μg/kg by subcutaneous route (M Phail index of 4.).

| Results: | | |
|---|---|---|
| Tests | | Average |
| HM + 10% ethanol, s/c | | 0 |
| Progesterone | 0,1 mg/kg, s/c | 1,8 |
| Progesterone | 1 mg/kg, s/c | 3,8 |
| Trimegestone | 0,003 mg/kg, s/c | 3,8 |
| Product B | 0,01 mg/kg, s/c | 1,4 |
| Product B | 0,1 mg/kg, s/c | 2 |
| Product B | 1 mg/kg, s/c | 3,8 |
| Product A | 0,01 mg/kg, s/c | 3,8 |
| Product A | 0,1 mg/kg, s/c | 3,8 |
| Product A | 1 mg/kg, s/c | 3,8 |
| Product A | 1 mg/kg, per os | 4 |

The averages were produced for the uterine lace (McPhail Index).

Conclusion:

This Clauberg-McPhail test showed a good progestomimetic activity for Product B at 1 mg/kg (McPhail: index 3.8). Product A was just as active starting from the dose of 0.01 mg/kg (McPhail index: 3.8) and at 1 mg/kg p/o route expressed a better activity than s/c route (McPhail index: 4 versus 3.8 and stronger hypertrophy of the cornua). Furthermore, histological observation of sections of the uterus did not reveal morphological anomalies.

Various modifications of the compositions and method of the invention may be made without departing from the spirit or scope thereof and it is to be understood that the invention is intended to be limited only as defined in the appended claims.

What is claimed is:

1. A compound of the formula

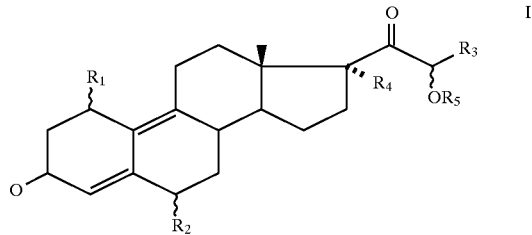

wherein $R_1$ is hydrogen and $R_2$ is —$OR_6$ or $R_1$ is —$OR_6$ and $R_2$ is hydrogen and $R_6$ and $R_5$ are individually selected from the group consisting of acyl of an organic carboxylic acid of 1 to 12 carbon atoms optionally substituted by at least one halogen and hydrogen and $R_3$ is alkyl of 1 to 12 carbon atoms, $R_4$ is alkyl of 1 to 4 carbon atoms, the wavy lines indicate the α- or β-position and that —$OR_5$ is in the 21R or 21S-position.

2. A compound of claim 1 wherein $R_3$ and $R_4$ are methyl.

3. A compound of claim 1 wherein $R_1$ is hydrogen and $R_2$ is hydroxy.

4. A compound of claim 1 wherein $R_1$ is hydroxy and $R_2$ is hydrogen.

5. A compound of claim 1 selected from the group consisting of [17β-(S)]-1-hydroxy-17-(2-hydroxy-1-oxopropyl)-17-methyl-$\Delta^{4,9}$-estradiene-3-one and [17β-(S)]-6-hydroxy-17-(2-hydroxy-1-oxopropyl)-17-methyl-$\Delta^{4,9}$-estradiene-3-one in any one of 1α-OH, 1β-OH, 6α-OH or 6β-OH stereoisomeric configurations or mixtures thereof.

6. A composition comprising a compound of claim 1 and an estrogen compound.

7. A composition of claim 6 wherein the estrogen compound is 17β-estradiol.

8. A process for the preparation of a compound of claim 1 comprising subjecting a compound of the formula

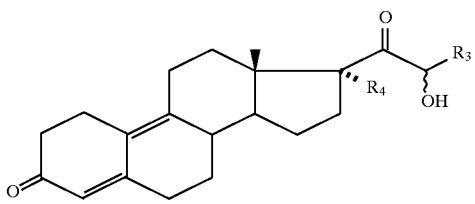

wherein $R_3$, $R_4$ and the wavy lines are defined as in claim 1 to a bioconversion by culturing with filamentous fungi and optionally separating out the 1-OH and 6-OH products or esterifying the hydroxylated compounds.

9. The process of claim 8 wherein the filamentous fungi are selected from the group consisting of *Cuninghamella baineri* ATTC 9244, *Mortierella isabellina*, NRLL 1757 or MMP 108 and *Fusarium roseum* ATCC 14717.

10. The process of claim 8 wherein the compound of formula II is[17β-(S)]-17-(2-hydroxy-1-oxopropyl)-17-methyl-$\Delta^{4,9}$-estradiene-3-one.

11. The process of claim 10 wherein the fungi is selected from the group consisting of *Cuninghamella baineri, Mortierella isabellina* and *Fusarium roseum* to obtain a mixture of [17β-(S)]-1-hydroxy-17-(2-hydroxy-1-oxopropyl]17-methyl-$\Delta^{4,9}$-estradiene-3-one and 17β-(S)]-6-hydroxy-17-(2-hydroxy-1-oxopropyl)-1-methyl- $\Delta^{4,9}$-estradiene-3-one and separating the mixture.

12. The process of claim 10 wherein the fungi is *Cuninghamella baineri* ATTC 8244 to obtain [1α, 17β-(S)]-1-hydroxy-17-(2-hydroxy-1-oxopropyl)-17-methyl-$\Delta^{4,9}$-estradiene-3-one or [1β-17β-(S)]-1-hydroxy-17-(2-hydroxy-1-oxopropyl)-$\Delta^{4,9}$-estradiene-3-one.

13. A progestomimetic composition comprising a progestomimetically effective amount of a compound of claim 1 and a pharmaceutical carrier.

14. A progestomimetic composition comprising a progestomimetically effective amount of a compound of claim 5 and a pharmaceutical carrier.

15. A method of inducing progestomimetic activity in warm-blooded animals comprising administering to warm-blooded animals a progestomimetically effective amount of a compound of claim 1.

16. A method of inducing progestomimetic activity in warm-blooded animals comprising administering to warm-blooded animals a progestomimetically effective amount of a compound of claim 5.

* * * * *